United States Patent [19]
Bark et al.

[11] Patent Number: 5,522,403
[45] Date of Patent: Jun. 4, 1996

[54] SPLASH SHIELD

[75] Inventors: Jeffrey E. Bark, Green Bay, Wis.; William E. Potts, Tallahassee, Fla.

[73] Assignee: Microtek Medical, Inc., Columbus, Miss.

[21] Appl. No.: 222,624

[22] Filed: Apr. 4, 1994

Related U.S. Application Data

[63] Continuation-in-part of Ser. No. 145,068, Oct. 27, 1993, abandoned, which is a continuation of Ser. No. 967,936, Oct. 28, 1992, Pat. No. 5,305,765, which is a continuation of Ser. No. 760,176, Sep. 16, 1991, abandoned.

[51] Int. Cl.$^6$ ..................................................... A61F 13/00
[52] U.S. Cl. ............................................ 128/849; 128/853
[58] Field of Search ..................................... 128/849, 850, 128/851, 852, 853, 854, 855, 856

[56] References Cited

U.S. PATENT DOCUMENTS

| | | | |
|---|---|---|---|
| 4,520,807 | 6/1985 | Rotter | 128/849 |
| 4,572,173 | 2/1986 | Comeau | 128/849 X |
| 4,607,631 | 8/1986 | Hanssen | 128/853 |
| 4,903,170 | 2/1990 | Jessamine et al. | 128/852 X |
| 4,966,168 | 10/1990 | Glassman | 128/849 X |
| 5,127,413 | 7/1992 | Draeger | 128/849 |
| 5,140,997 | 8/1992 | Glassman | 128/849 |

FOREIGN PATENT DOCUMENTS 8806032  8/1988  WIPO ................................... 128/849

*Primary Examiner*—Sam Rimell
*Attorney, Agent, or Firm*—Baker & Botts

[57] ABSTRACT

A surgical splash shield for use in surgical procedures requiring the use of a surgical scope such as an endoscope. In one embodiment, the device is generally rectangular in shape with a hole or an eyepiece port having an elliptical hole located at the center and uses adhesive tape to secure the device. In another embodiment, the device comprises a relatively square section which protects the clinician's body and a circular area which covers the scope and protects the clinician's face. The device, again, has an elliptical eyepiece port and is secured by adhesive tape.

8 Claims, 3 Drawing Sheets

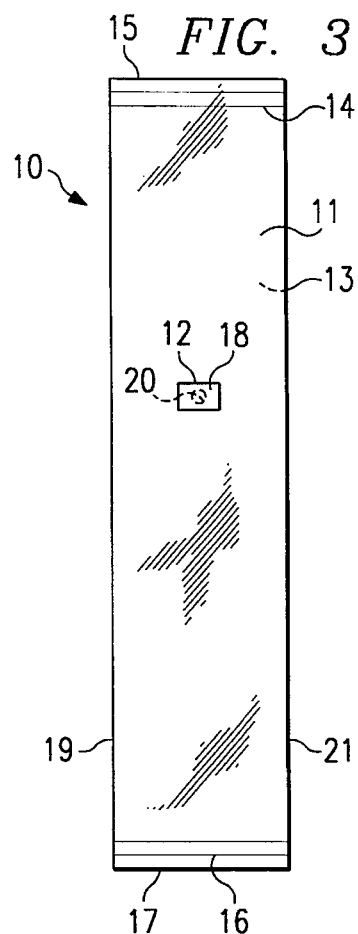
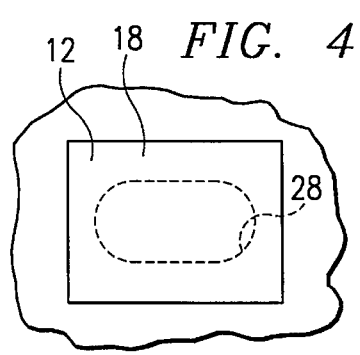
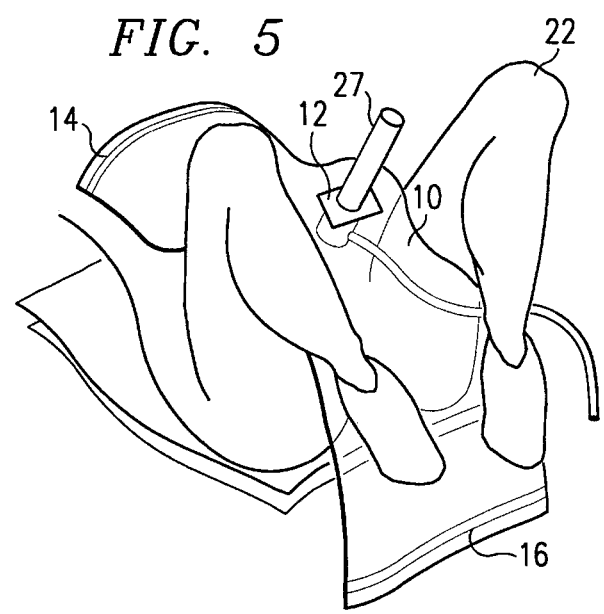
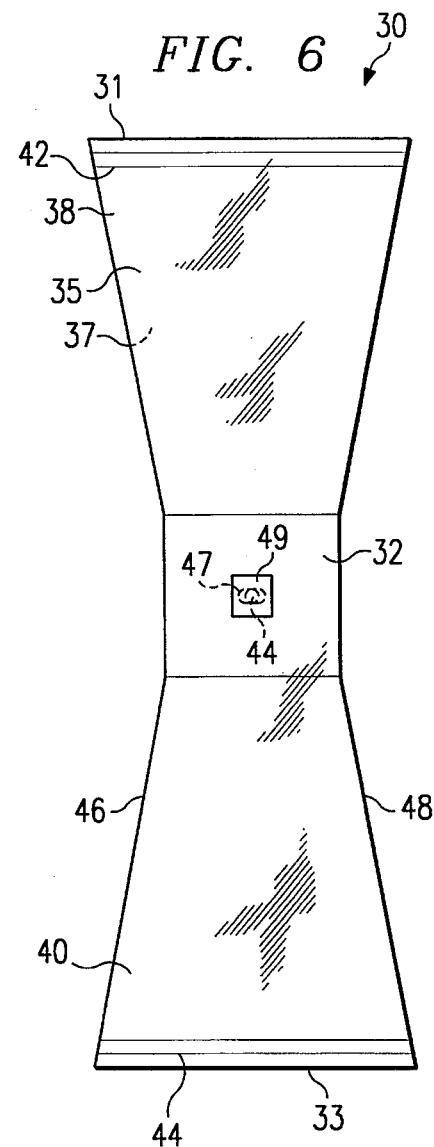

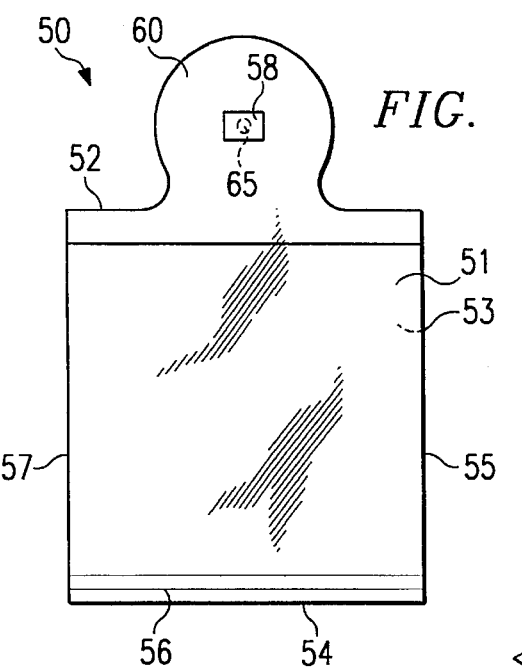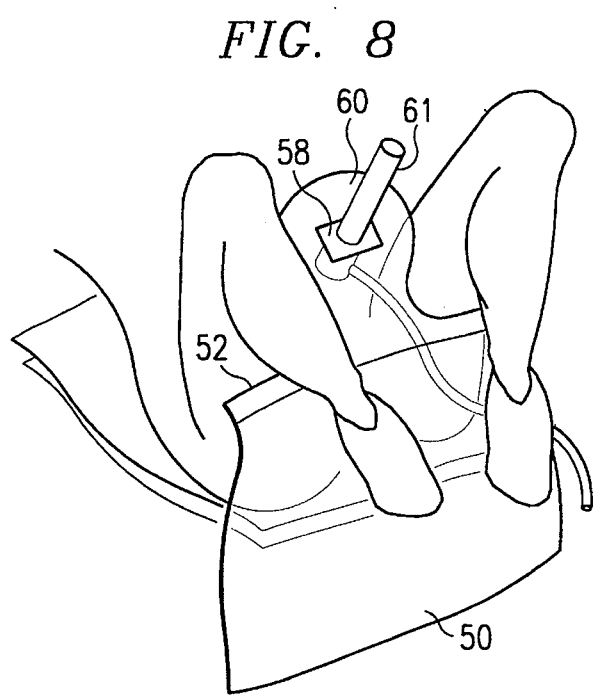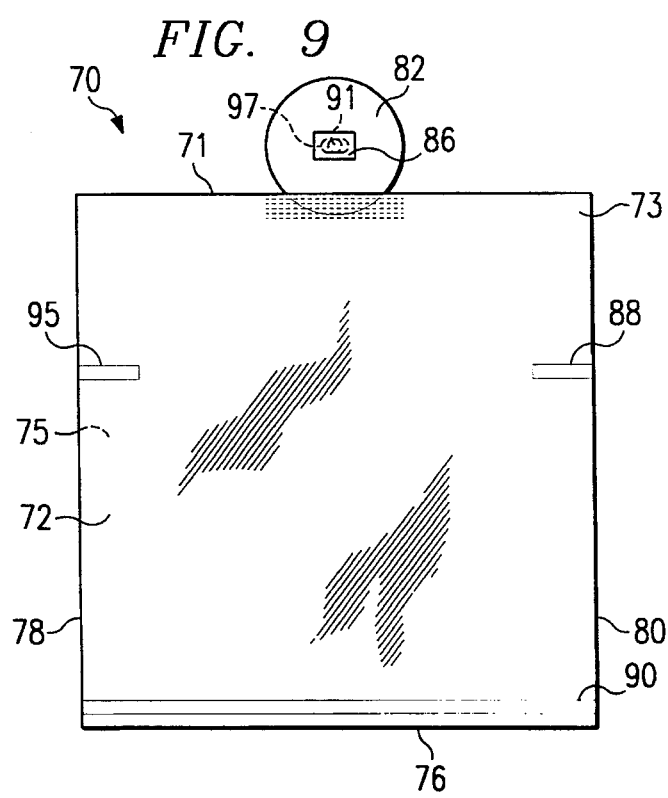

SPLASH SHIELD

Application is a continuation-in-part of U.S. patent application Ser. No. 08/145,068, filed Oct. 27, 1993, now abandoned, which is a continuation of U.S. patent application Ser. No. 07/967,936, filed Oct. 28, 1992, now U.S. Pat. No. 5,305,765, which a continuation of U.S. patent application Ser. No. 07/760,176, filed Sep. 16, 1991, now abandoned.

BACKGROUND OF THE INVENTION

With the advent of highly contagious diseases such as AIDS, Hepatitis B and Hepatitis C, the Occupational Safety and Health Administration (OSHA) has developed strict regulations as to the use of personal protective equipment in the clinical setting. While various face shields, masks, gowns and other devices are available to meet these guidelines and better protect the clinician and his staff, there is a need to provide a device that will specifically protect a physician while performing a procedure in which a surgical scope and other related surgical instruments are used.

The prior art has concentrated on protecting sterile, prepared areas of the patient from contamination by non-sterile areas (see, for example, U.S. Pat. Nos. 4,414,968 (Amin); 4,462,396 (Wickman); 4,378,794 (Collins); 4,489,720 (Morris, et el.); 4,809,628 (Jackson); 4,974,604 (Morris)). But efforts to protect the physician from contaminated body fluids have been unsatisfactory.

In U.S. Pat. No. 4,834,068, for example, Gottesman discloses a disc-shaped, rigid plastic splash shield that attaches to the eyepiece of an endoscope or similar instrument, providing some protection for the physician's face. Splashing blood or irrigation fluid simply rebounds from the rear face of the splash shield and drips onto the floor, or runs down the surface of a conventional surgical drape, or off of the physician's clothing. U.S. Pat. No. 4,848,322 (Dash, et al.) discloses a similar rigid face shield, which is rectangular and curved slightly to wrap around the physician's face. Also, U.S. Pat. No. 4,535,481 (Ruth-Larson, et al.) discloses a protective gown with a broad skirt and fluid-impermeable areas that can be worn by the physician for protection during high-fluid procedures.

Aside from these prior art devices, the only protection afforded the physician by prior art devices consists of channelling blood and irrigation fluids, and sometimes feces, into disposal bags, or into a trough and drain arrangement sometimes provided on operating tables used for procedures such as cystoscopies. See, for example, U.S. Pat. No. 4,378,794 (Collins); U.S. Pat. No. 4,903,710 (Jessamine, et al.); and U.S. Pat. No. 4,471,769 (Lockhart). U.S. Pat. No. 4,926,882 (Lawrence) discloses a clear plastic bag intended to protect a physician conducting an autopsy from body fluids, blood, and bone fragments dispersed in the air by an oscillating bone saw. It would be incapable of use on live patients.

In short, the prior art intended for use with live patients teaches only small, rigid masks and complex drapes which are usable only for certain specific surgical procedures, and provide inadequate protection and which allow only partially-protected access to the patient. Our invention is directed to overcoming the aforementioned limitations and problems in prior art devices.

SUMMARY OF THE INVENTION

Our invention provides new advantages not found in currently available devices. Furthermore, our invention overcomes many of the disadvantages of currently available splash shields and drapes.

One embodiment of our invention relates to a splash shield formed from an impermeable plastic sheet of substantially rectangular shape, with an adhesive strip near one or both opposing edges suitable for attachment directly to the patient's torso, or to a conventional drape of the sort used for any high-fluid surgical procedures, such as uro-genital or rectal surgery. The splash shield may be pierced by an aperture or a hole located at the apex of two lines of perforated tear slits oriented at right angles to each other. An eyepiece port located on the splash shield may also be used. Other embodiments shaped to conform specifically to parts of the patient's body are also disclosed.

Since many optical instruments, such as endoscopes, have eyepieces shaped like the bell of a trumpet, the hole should be either oval or elliptical in shape and suitably sized to fit over the eyepiece. Using an oval or elliptical hole allows the expanded bell of such an instrument to be inserted through the hole from the bottom side by stretching the hole, and when the material relaxes, the hole is fully occluded by the bell of the endoscope. Alternatively, a variety of adhesive, Velcro®, elastic, or mechanical attachment means can be used at the location of the hole to seal the splash shield drape around the instrument eyepiece.

In the simplest embodiment of our invention, the splash shield of our invention includes a flexible plastic sheet of a size that is sufficient to cover the area of the patient upon which the operation is to be performed. A substantial overlap around the edges of the operating area is desired. The bottom side of the plastic sheet near its top edge carries an adhesive fastener which engages with the patient's body to secure the splash shield in place. A sealable aperture is present in the plastic sheet or eyepiece port for accommodating the eyepiece of an optical instrument. This embodiment (and others) provides protection from splashing liquid while permitting continued normal use of optical instruments.

In use, the splash shield of our invention covers the operating area, shielding the physician from splashing blood or irrigation fluid. The physician obtains manual access to the operating area simply by inserting his or her hands underneath the side or bottom edges of the splash shield. The shield can be made of a flexible or rigid, transparent plastic, allowing a view of the operating area. As a result, excellent protection without obstruction of the use of optical instruments can be achieved with our invention.

Accordingly, an object of our invention is to provide a splash shield for use in any surgical operation.

An additional object of our invention is to provide a splash shield with the ability to accommodate optical instruments while maintaining a high level of splash protection.

A further object of our invention is to provide a splash shield that may be used to protect a physician during a cystoscopy.

Another object of our invention is to provide a splash shield that is of a shape suitable for accommodation of optical instruments such as endoscopes during a cystoscopy.

Still another object of our invention is to provide a splash shield shaped to conform to specific parts of the patient's body.

Other advantages of our invention will become apparent from the drawings, detailed description and claims which follow:

DESCRIPTION OF THE DRAWINGS

The novel features of our invention are set forth with particularity in the appended claims. Our invention, together with its objects and the advantages thereof, may best be understood by reference to the following description taken in conjunction with the accompanying drawings:

FIG. 3 is a plan view of a splash shield having a sealable eyepiece port and two attachment strips;

FIG. 4 is a detailed view of the sealable eyepiece port with dashed lines representing a movable flap made from a partial cut in the material;

FIG. 5 is a perspective view showing how the splash shield shown in FIG. 3 is positioned on a patient;

FIG. 6 is a plan view of another, composite splash shield showing the arrangement of the individual sections;

FIG. 7 is a plan view of yet another composite splash shield having a disc-shaped area for covering the surgical scope and protecting the clinician's face as well as an attached section for protecting the clinician's person;

FIG. 8 is a perspective view showing how the embodiment shown in FIG. 7 is positioned on a patient; and FIG. 9 is a plan view of a variation on the embodiment shown in FIG. 7, but in composite form with a separate disc-area and relatively square section.

DETAILED DESCRIPTION OF THE EMBODIMENTS

Figure 1:
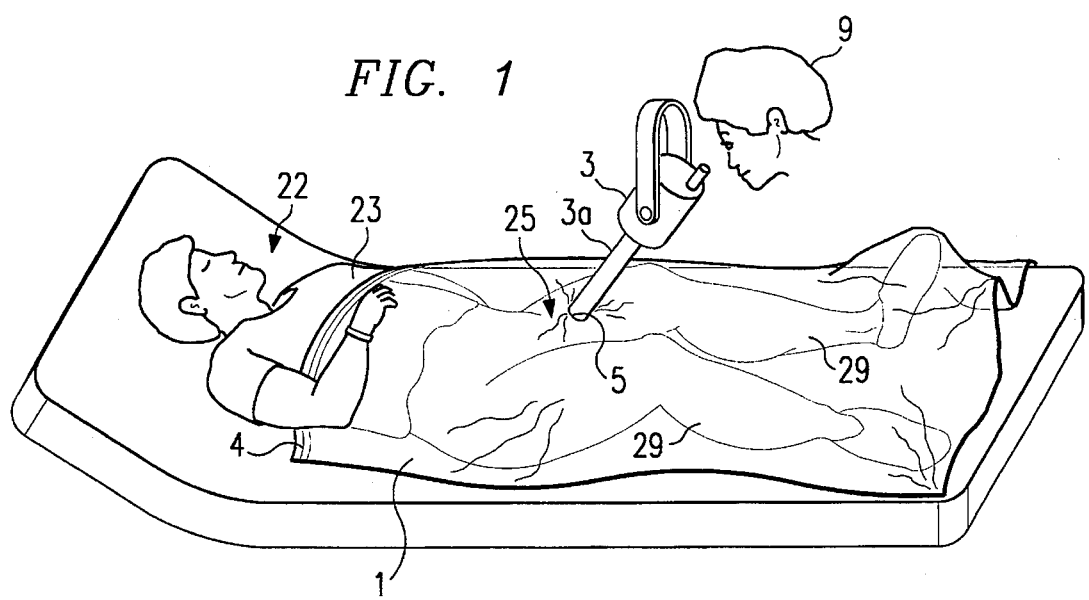
FIG. 1 is a perspective view of our splash shield positioned over a patient.

FIG. 1 shows the splash shield 1 in position over a patient 22, in which an operation on the patient's groin area is to be performed. Top portion 2a of plastic sheet 2 is affixed to torso 23 of patient 22 during surgery via hypoallergenic pressure sensitive tape 4. Once affixed to the torso 23 of patient 22, the remaining portion of splash shield 1 is draped over groin area 25 which is to undergo surgery. Once draped over groin area 25, the remaining lower portion 2b of plastic sheet 2 may be further draped between and over patient's legs 29.

Once in place, splash shield 1 is ready to receive and accommodate a medical optical instrument 3 such as a cystoscope or endoscope, or any other suitable surgical instrument such as a catheter. Instrument 3 is inserted through hole 5 in plastic sheet 2. Instrument 3 is secured in place with the assistance of perforations 6 which provide a snap fit over eyepiece 3a of hole 5, adhesive tape 6 is wrapped around the circumference of eyepiece 3a which is surrounded by plastic material immediately around hole 5. The result is a fluid-tight seal around eyepiece 3a.

With instrument 3 in place with top portion 2a of plastic sheet affixed to torso 23 of patient 22 and lower portion 2b draped over and between patient's legs 29 (or over any other operating ares of the patient), the physician is ready to begin surgery on patient 22. The area subject to surgery will be beneath splash shield 1. In the event that fluids (not shown) splash up out of the area under surgery, physician 9 will be protected. The splashed fluids are directed back toward patient 22 to later be absorbed and/or channeled away.

Figure 2:
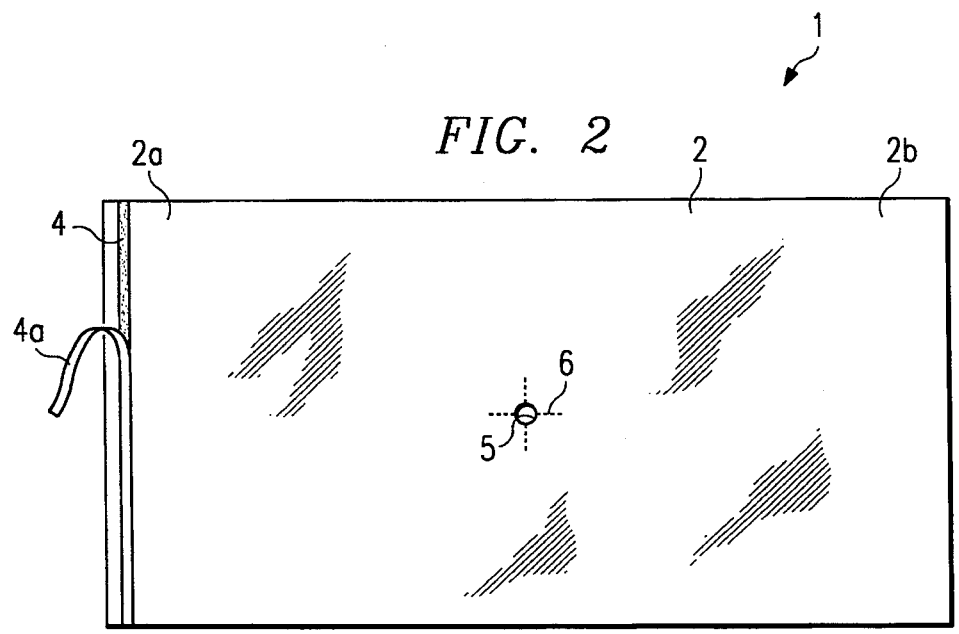
FIG. 2 is a top view of the simplest embodiment of our splash shield.

Turning to FIG. 2, the splash shield 1 is shown laid completely flat. The splash shield 1 includes flexible plastic sheet 2 which forms the overall shape of the splash shield 1. This plastic sheet 2 may be manufactured in various sizes according to the requirements of the surgery to be undertaken. The size of plastic sheet 2 may be tailored according to the size of the patient 22 as well. For most operations, it is preferable that the plastic sheet 2 be approximately 58 inches long and approximately 26 inches wide. Such an overall size of the splash shield 1 can be used in most surgeries.

To adequately repel fluids and resist minor punctures during surgery, it is preferred that the plastic sheet 2 be of at least 1 mil in thickness and that it be manufactured of transparent polyethylene, polypropylene or the like. The overall shape of plastic sheet 2 is preferably rectangular, but may be custom tailored according to the location and type of surgery to be conducted.

Splash shield 1 has an adhesive layer 4 to secure splash shield 1 to patient 22 which preferably extends the entire width of plastic sheet 2. Adhesive layer 4 carries a release liner 4a which is to remain on adhesive layer 4 until splash shield 1 is to be used. When it is time for splash shield 1 to be used for surgery, release liner 4a is removed from adhesive layer 4. Entire splash shield 1 is turned over so the side with adhesive layer 4 is facing patient's torso 23. Splash shield 1 is moved in to the desired position where pressure is then applied to the back of splash shield 1 in the area of adhesive layer 4 to secure splash shield 1 to patient's torso 23. Next, the remaining portion of splash shield 1 is draped over the lower half of the patient's body.

Referring to FIG. 2, hole 5 is cut in plastic sheet 2. Perforations 6 are included as tear slits to allow a snap fit over instrument eyepiece 3a. Hole 5 may be generally circular in shape; however, hole 5 can be other shapes, such as oval or rectangular, to accommodate eyepieces of varying cross-sectional shapes.

FIG. 3 shows another embodiment of our invention having a sealable eyepiece port 12. This embodiment comprises sheet 10, eyepiece port 12, and oppposingly located adhesive layers 14 and 16. Sheet 10 has a top surface 11, bottom surface 13, upper edge 15, lower edge 17, and opposing side edges 19 and 21. Hole 20 of eyepiece port 12 can either be cut from sheet 10 or formed from a reinforcement member 18, which has been attached to sheet 10.

In use, as shown in FIG. 5, sheet 10 is attached to patient 22 by adhesive layer 14, which is located near upper edge 15 on bottom surface 13. Adhesive layer 14 should be attached near a patient's navel. Adhesive layer 16, which is located near lower edge 17 on bottom surface 13, may be optionally attached to surgical table or a surgical tray (not shown). Since sheet 10 may be placed between a patient's legs and may be attached near the navel and to a table, it has been found that the appropriate width and length of sheet 10 may be approximately 12"×56", respectively. Of course, other widths and lengths are also contemplated by our invention.

A surgical endoscope 27 or other instrument is next placed through hole 20 of eyepiece port 12 which is located on the centerline of sheet 10 and over the surgical site. The clinician operates endoscope 27 by placing his gloved hands under sheet 10, keeping sheet 10 between himself and fluids from patient 22. Any spray or splash of fluid will hit bottom surface 13 of sheet 10 and fall toward patient 22. Should the clinician desire, sheet 10 can be oriented so that any fluids could be directed by sheet 10 into a collection device such as a funnel or tray.

The material used to form sheet 10 in this embodiment is necessarily transparent and flexible. One such material is low density polyethylene in a thickness of six mils (0.006"). Adhesive layers 14 and 16 can be a double-sided adhesive tape which provides a secure hold as previously described. One such tape is Coating Sciences Incorporated's RX264S. Reinforcement membrane 18 which includes eyepiece port 12 must be necessarily flexible and siongable. One such suitable material is 3M Company's #1772 polyethylene tape.

Hole 20 of eyepiece port 12 may be elliptical in plan view. The elliptical shape allows the passage of the bell portion of an endoscope eyepiece without undue stress to the surrounding area. The perforations 6, illustrated in FIG. 2, may be omitted. Alternately, hole 20 and eyepiece port 12 can be an annular disc of latex.

As shown in FIG. 4, a flap of material 28 may also be left in the center of the eyepiece port 12 which covers hole 20. As further shown by the dashed lines in FIG. 4, flap 28 can be formed by cutting an incomplete outline of hole 20 in sheet 10 or membrane 18 or by separately attaching a piece of material. Flap 28 is intended to return to the closed position in the event that the scope is removed during the procedure. This will help to prevent additional leakage through what would have been an open orifice through sheet 10.

FIG. 6 illustrates another embodiment of our invention. This embodiment is a composite shield 30 comprised of center section 32, and end sections 38 and 40. When these sections are combined they form a shield having top surface 35, bottom surface 37, upper edge 31, lower edge 33, and opposing outer edges 46 and 48. This embodiment further includes adhesive layers 42 and 44 located on bottom surface 37 near upper edge 31 and lower edge 33, respectively. Located in center section 32 is sealable eyepiece port 49 which further includes hole 44. Flap 47 covers hole 44 when no instrument is being used. Opposing outer edges 46 and 48 of shield 30 can be inwardly tapered so as to offer the clinician easier access to the area beneath shield 30. This embodiment may also be oriented in such a way as to direct the fluid into a container or tray.

The materials making up the composites should be transparent and can be the same as those suggested previously. Alternatively, a more rigid yet transparent material such as acrylic may be used for center section 32. Hole 44 of eyepiece port 49 may be elliptical in shape as previously described. Flap 47 can either be separately attached or formed by a partial cut in center section 32. End sections 38 and 40 may be joined to center section 32 by a number of methods, including but not limited to, adhesive, heat seal, RF weld or other mechanical means.

The operation and placement of this embodiment is generally the same as the embodiment shown in FIG. 3. The sizing is slightly different than described above. It is suggested that the overall length be 60" and the tapered ends start out at a width of 24" and reduce down to 12".

Another embodiment of our invention is illustrated in FIG. 7. This embodiment includes a shield 50 having a top surface 51, bottom surface 53, upper edge 52, lower edge 54 and opposing side edges 55 and 57. Upper edge 52 has been radially sculpted to form disc-shaped member 60. This embodiment further includes an adhesive layer 56 located on bottom surface 53 near lower edge 54, and a sealable eyepiece port 58 with an hole 65 in disc-shaped member 60.

Adhesive layer 56 is used for attachment to the table, tray or other drapes. As shown in FIG. 8, a surgical scope 61 provides the support for disc-shaped member 60 of shield 50. As further shown in FIG. 8, radially sculpted upper edge 52 and disc-shaped member 60 are shaped in such a way that disc-shaped member 60 fits between a patient's legs and eyepiece port 58 and hole 60 are located over the surgical site.

The clinician may then place his or her arms in the radiused areas below the ensuing substantially disc-shaped member 60, which provides easy access beneath shield 50. Disc-shaped area 60 provides the protection for the clinician's face while the remainder of shield 50 provides protection for the rest of his person. Shield 50 may also be oriented to direct fluid into a container or tray.

To provide adequate protection, it is suggested that disc-shaped member 60 have a 6" radius and the remainder of sheet 50 be 24" in width and 27" in length. The materials used to form shield 50 are the same as described for other embodiments. The design and orientation of eyepiece port 58 is also the same as described above.

Another embodiment, shown in FIG. 9, provides a composite shield 70, which includes sheet 72 having top surface 73, bottom surface 75, upper edge 71, lower edge 76, and opposing side edges 78 and 80. Attached to upper edge 71 of sheet 72 is disc 82, which further includes sealable eyepiece port 86 and hole 91. Located on bottom surface 75 near upper edge 71 and perpendicular to opposing side edges 78 and 80 are first adhesive layers 88 and 95. A second adhesive layer 90 is located on bottom surface 75 near lower edge 76. Sheet 72 can be made of the same transparent polyethylene material discussed above and disc 82 can be attached to sheet 72 by a number of known methods including, but not limited to adhesive, heat seal, RF weld or other mechanical means.

The operation and sizing of this embodiment is generally the same as the embodiment shown in FIG. 7. Disc 82, however, is necessarily made from a more rigid, transparent material, such as acrylic. Eyepiece port 86 is illustrated as an annular disc of latex, but can also be an elliptical design as described in the previous embodiments. Eyepiece port 86 may also include a flap 97 of the same construction as described above.

Our invention also contemplates embodiments in which more than one eyepiece port or surgical instrument port may be provided in the device and, in some cases, a reinforcement may not be used. In all embodiments, the size, number and location of the eyepiece port and actual size of the shield used is dependent on the final procedure for which the specific device is to be designed.

It should be understood that various changes and modifications to the preferred embodiments described would be apparent to those skilled in the art. Such changes and modifications can be made without departing from the spirit and scope of our invention and without diminishing its intended advantages. It is, therefore, intended that such changes and modifications be covered by the following claims.

We claim:

1. A splash shield comprising:
   a sheet having a top upper surface, a bottom surface, an upper edge, a lower edge and opposing side edges;
   an eyepiece port formed from a hole in said sheet;

said upper edge formed to define a disc-shaped area; and an adhesive layer located on said bottom surface near said lower edge.

2. The device of claim 1 wherein said sheet is made from a transparent material.

3. The device of claim 1 wherein said hole is elliptical in shape.

4. The device of claim 1 wherein said eyepiece port includes a movable flap which covers said hole.

5. A splash shield comprising:

a sheet having a top surface, a bottom surface, an upper edge, a lower edge, and opposing side edges;

a disc-shaped member which has been integrally attached to said upper edge of said sheet;

a sealable eyepiece port formed from an hole in said disc; and an adhesive layer located on said bottom surface near said lower edge.

6. The device of claim 5 wherein said disc-shaped member is made from a transparent material.

7. The device of claim 5 wherein said hole is elliptical in shape.

8. The device of claim 5 wherein said sealable eyepiece port includes a movable flap which covers said hole.

* * * * *